(12) United States Patent
Kaga

(10) Patent No.: US 7,705,329 B2
(45) Date of Patent: Apr. 27, 2010

(54) CHARGED PARTICLE BEAM PROCESSING APPARATUS

(75) Inventor: Hiroyasu Kaga, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 161 days.

(21) Appl. No.: 12/124,776

(22) Filed: May 21, 2008

(65) Prior Publication Data

US 2008/0290291 A1 Nov. 27, 2008

(30) Foreign Application Priority Data

May 22, 2007 (JP) ............... 2007-136028

(51) Int. Cl.
*H01J 37/26* (2006.01)
(52) U.S. Cl. ............... 250/492.21; 250/492.2
(58) Field of Classification Search ........... 250/492.21, 250/492.2, 492.1
See application file for complete search history.

(56) References Cited

U.S. PATENT DOCUMENTS 5,969,357 A * 10/1999 Todokoro et al. ............ 850/9

FOREIGN PATENT DOCUMENTS

| JP | 5-52721 A | 3/1993 |
| JP | 2002-503870 A | 2/2002 |
| WO | WO 99/41765 A1 | 8/1999 |

OTHER PUBLICATIONS

"When Preparing Sample for TEM Using Focused Ion Beam", Surface Science: vol. 16, No. 12, pp. 755-760, 1995.
THORU ISHITANI et al., "Transmission Electron Microscope Sample Preparation Using a Focus Ion Beam", J Electron Microscope vol. 43, pp. 322-326, 1994.
YASUNORI YAMAMURA et al., "Energy Dependence of Ion-induced Sputtering Yields Monatomic Solids At Normal Incidence", At. Dat & Nuc Dat. Tab. vol. 62, pp. 149-253 (1996).

* cited by examiner

*Primary Examiner*—Kiet T Nguyen
(74) *Attorney, Agent, or Firm*—Crowell & Moring LLP

(57) ABSTRACT

In view of the fact that in line processing, when processing is performed to a certain depth, the processing does not advance with the passage of a further processing time, a processing apparatus is provided which can appropriately control the depth of grooves in linear groove processing and perform the processing at high speed. A line width and line depth are calculated so as to minimize a processing time of processing on a line to a required depth and processing is performed using the width and line depth as set values of processing. Furthermore, processing is performed with the area in which the beam is actually irradiated superimposed on the scanned image of a focused ion beam and displayed on a screen. In the case of an ion beam inclined with respect to the sample surface, processing is also performed by displaying the area where the beam is actually irradiated by taking the inclination of the sample with respect to the beam into consideration.

16 Claims, 10 Drawing Sheets

(a)

(b)

Angle of inclination of observed cross section is 45°

Cross section of line processing, line width 1.5 μm

Processing depth h and aspect ratio (H/W)

Aspect ratio (H/W) of setting and aspect ratio (h/w) of processing result

Calculation model

Aspect ratio X and
( accumulated amount of Qlost /total flux of hole ) ratio

Aspect ratio (H/W) of setting
and aspect ratio (h/w) of processing result $L' = L/\cos\theta$ $d = h/\cos\theta$ $W' = W/\cos\theta$

CHARGED PARTICLE BEAM PROCESSING APPARATUS

BACKGROUND OF THE INVENTION

1. Field of the Invention

The present invention relates to a charged particle beam processing apparatus, and relates, for example, to a charged particle beam processing apparatus that processes, when processing grooves linearly, a sample by forming the grooves to a desired depth in the sample.

2. Background Art

Transmission electron microscopes generally require thin lamina having a thickness on the order of 0.1 μm as samples. According to a conventional method, a micro piece including observation locations is cut out from a sample, thinned by means of mechanical polishing and then a thin lamina having a thickness on the order of 0.1 μm is created using an ion milling apparatus.

In recent years, focused ion beams are being more and more used to create such thin samples. Enabling observation and processing, a focused ion beam apparatus can create a thin sample including desired observation locations processed to a size on the order of 10 μm and a thickness on the order of 0.1 μm.

Therefore, when observing, for example, a semiconductor device using a transmission electron microscope, the use of a focused ion beam makes it possible to identify observation locations and create a thin sample including the observation locations. Such a sample creation method using a focused ion beam is reported in Non-Patent Documents 1 and 2.

Furthermore, Patent Document 1 discloses an apparatus and method for focused ion beam processing using a column which is inclined with respect to a wafer and a rotation function of a stage. Furthermore, Patent Document 2 describes a method (sampling method) of cutting out a thin-lamina sample piece using a focused ion beam and a sampling probe.

[Patent Document 1] JP Patent Publication (Kohyo) No. 2002-503870

[Patent Document 2] JP Patent Publication (Kokai) No. 5-52721

[Non-Patent Document 1] "When Preparing Sample for TEM Using Focused Ion Beam" Surface Science Vol. 16, No. 12, pp 755-760, 1995

[Non-Patent Document 2] "Transmission Electron Microscope Sample Preparation Using a Focused Ion Beam"; J Electron Microscope 43, pp 322-326, 1994

[Non-Patent Document 3] Yamamura, Y., "Energy Dependence Of Ion-induced Sputtering Yields From Monatomic Solids At Normal Incidence," At.Dat, &Nuc.Dat.Tab.62 (1996) 149)

SUMMARY OF THE INVENTION

However, recent semiconductor devices have a fine structure and when one attempts to analyze a specific region, one cannot make any analysis without being familiar with a high level semiconductor process technique and structure thereof. A defect size also falls below 100 nm and it is not possible to judge the presence or absence of defects without having knowledge to make a subtle distinction between the presence and absence of defects. When such defects exist, it is difficult to identify their observation locations and it is thereby impossible to directly process desired observation locations using a focused ion beam apparatus. For this reason, such a method is adopted that the perimeter of a micro piece area containing defects is processed using a focused ion beam apparatus, extracted from the wafer (hereinafter referred to as "sampling"), then placed on a sample carrier and transformed to a thin lamina on the sample carrier for an analysis.

In such thin-lamina processing for a defect analysis, realizing reliable thin lamina processing at target locations requires a tool capable of detecting a processing end point, for example, means for monitoring a processing condition capable of, for example, observing a cross section subject to thin lamina processing using a SEM. Furthermore, there can also be a necessity for carrying out processing and converting target observation locations to a thin lamina while moving the observation locations back and forth between a transmission electron microscope and a focused ion beam apparatus.

Furthermore, also for an electrical analysis using a probing apparatus, there are recently appearing a growing number of methods of sampling micro pieces including an element from a wafer and analyzing electrical characteristics of the device. In such a case, a small sampling piece having a large surface area is more advantageous for an electrical analysis of the element.

Conventionally, when a micro piece including a defect is extracted from a wafer using a focused ion beam, the perimeter of the defective location is processed and a small protrusion including the defect is formed. The micro piece is then separated from the wafer by cutting out the root of this protrusion along an inclined surface.

However, when sampling a relatively large piece using the conventional method, a disadvantage is that the processing volume increases and the processing time is extended. As one method of reducing the processing volume, the volume may be reduced by linearly processing contours of the small piece, but when processing the linear groove using a focused ion beam apparatus, there is a problem, although this is the basics of processing, that as the line width decreases, the processing does not advance and it is not possible to perform processing to a required depth in a short time.

The present invention has been implemented in view of such a circumstance and provides a charged particle beam processing apparatus capable of controlling the depth of grooves and realizing fast processing when processing the linear grooves.

In order to solve the above described problem, the present invention determines a line width and line depth through calculations so as to minimize a processing time for processing to a necessary depth of the line and performs the processing using the line width and line depth as set values of processing. Furthermore, the present invention superimposes the area actually irradiated with a beam on a focused ion beam scanned image and displays the area on a screen for processing. In the case of an ion beam which is inclined with respect to the sample surface, the present invention performs processing by displaying the area actually irradiated with a beam by taking the inclination of the sample with respect to the beam into consideration.

That is, the charged particle beam processing apparatus according to the present invention is a charged particle beam processing apparatus that processes a sample using a charged particle beam, including a stage that moves the sample in a desired axial direction, a charged particle beam column that radiates the charged particle beam onto the sample, a control section that controls the charged particle beam column, and a calculation section that calculates a set value of a depth H for line creation (V groove) and a set value of a width W for line creation (V groove) from an inputted desired line segment length L and a desired depth d (=depth viewed in an radiation direction) for line creation (V groove). The calculation section calculates a condition that minimizes a processing time t based on an arithmetic expression for a processing time t expressed by the depth H of the groove, width W of the V groove, length L of the V groove, sputtering yield Y(0) of matter and a beam current Ib and thereby obtains the set values H and W. Furthermore, the control section causes the charged particle beam to be radiated onto the surface of the sample based on the set values H and W and length L for line creation calculated by the calculation section so as to form the V groove on the surface of the sample.

The charged particle beam processing apparatus is further provided with a display control section that displays the process area in which the charged particle beam is radiated onto the sample, superimposed on the sample image on the display section based on the line width W and length L for line creation calculated from the desired line depth h (=height of the small piece to be cut out).

Further features of the present invention will be made clear with preferred embodiments for implementing the present invention and the attached drawings.

According to the present invention, it is possible to reliably perform processing on a line to a required depth in a short time. Furthermore, it is also possible to reliably cut out a micro sample from the sample surface in a short time (high speed).

Figure 1:
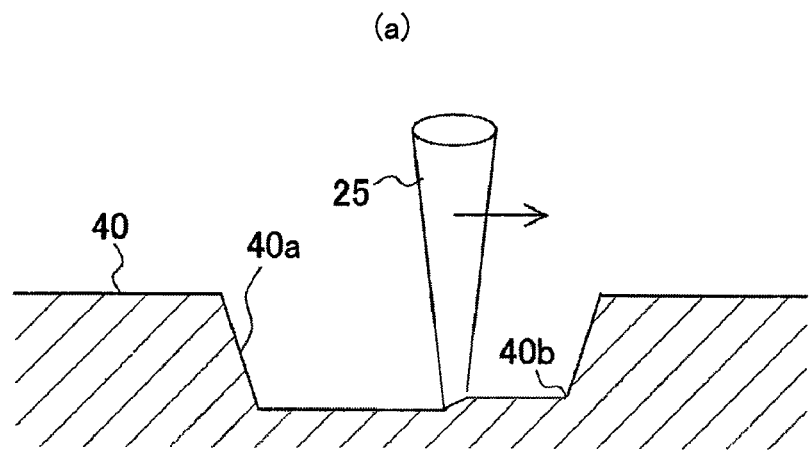
FIG. 1 illustrates a micro step on the sample surface and a beam radiation angle on a concave processing side produced by beam scanning.
Figure 1:
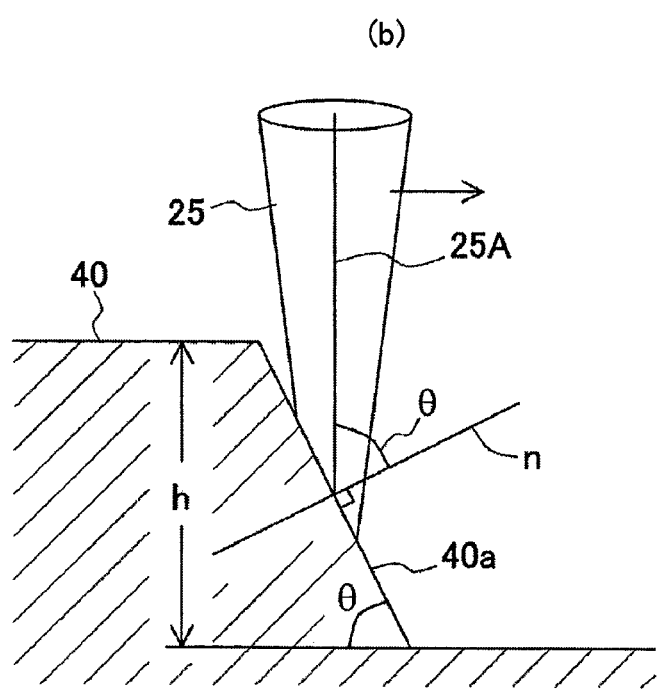

DESCRIPTION OF SYMBOLS 10 sampling manipulator
11 probe position control
12 sampling probe
20 focused ion beam (FIB) column
21 ion gun
22 beam limitation aperture
23 lens system
24 deflector
25 ion beam
30 deposition gun
31 nozzle
32 nozzle position/temperature controller
33 deposition source reservoir
40 wafer
41 wafer holder
42 stage
43 evacuator
45 charged particle detector
57 display control section
60 display

DETAILED DESCRIPTION OF THE PREFERRED EMBODIMENTS

With reference now to the attached drawings, an embodiment of the present invention will be explained below. However, it should be noted that this embodiment is not more than an example of implementing the present invention and is by no means intended to limit the present invention. Configurations common among the respective drawings will be assigned the same reference numerals.

<Processing Conditions: Principle of the Present Invention>

First, processing conditions when carrying out line processing using a focused ion beam of the present invention will be explained. As shown in FIG. 1(a), when an ion beam 25 scans the surface of a flat sample 40, an area at the ion beam irradiated point is shaved through sputtering according to the amount of irradiation, a difference in level is produced and a step is formed before and after beam scanning. At the turning point of beam scanning, the step is deepened between a portion irradiated with the beam and a portion not irradiated with the beam and a concave part is formed there. Therefore, inclined planes 40a and 40b are formed on the sample surface before and after ion beam scanning.

As shown in FIG. 1(b), when the angle of inclination of the inclined plane 40a is assumed to be θ, the angle which the normal n of the inclined plane 40a forms with an optical axis 25A of the ion beam 25 is defined as the angle of incidence of the beam. The angle of incidence of the beam is equal to the angle of inclination θ of the inclined plane 40a. Therefore, when the angle of inclination is 0 degrees, the angle of incidence of the beam becomes 0 degrees and when the angle of inclination is 90 degrees, the angle of incidence of the beam becomes 90 degrees.

Even when the ion beam is radiated in a direction perpendicular to the sample surface, since a micro step is formed, the ion beam irradiated plane is inclined and the angle of incidence of the ion beam does not become 0 degrees. The angle of incidence particularly increases at the turning points 40a and 40b of the scanning beam.

The sputtering yield by the ion beam (amount indicating how many atoms per one ion particle are sputtered) is a function of the angle of incidence of the ion beam. Yamamura proposes the following expression in Non-Patent Document 3 as a theoretical expression well accorded with experimental results.

[Formula 1]

$$Y(E,\theta) = Y(E) \cdot t^f \cdot e^{-S(t-1)} \quad \text{(Expression 1)}$$

Figure 2:
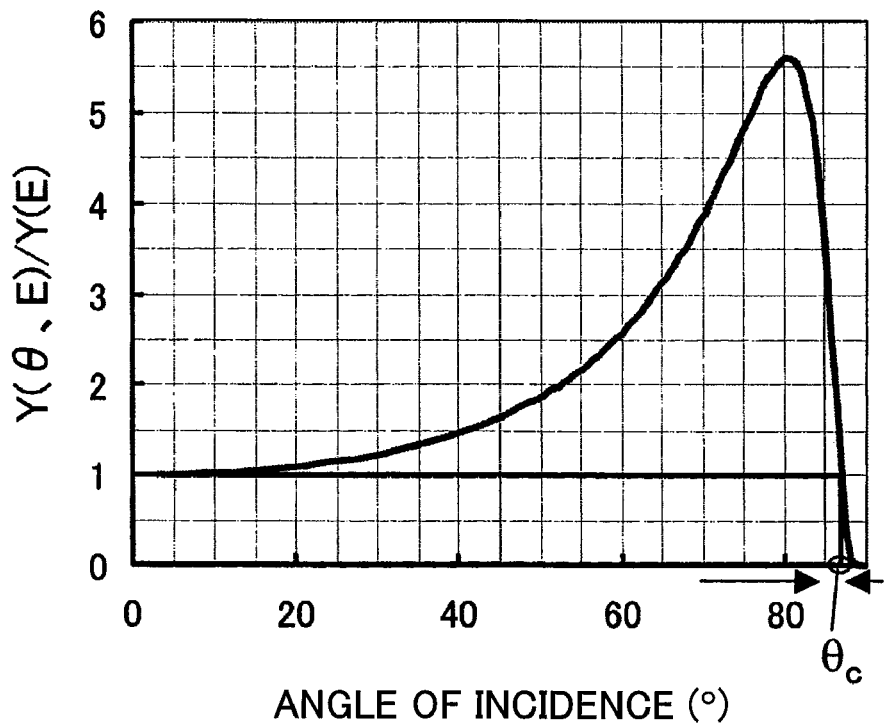
FIG. 2 shows angle of incidence dependency of sputtering yield.

Here, $t=1/\cos\theta$, and f and s are parameters. The curve in FIG. 2 is a graph when the parameters are assumed to be $f=1.8$, $s=0.3$ in Expression 1. The horizontal axis shows an angle of incidence of the ion beam and the vertical axis shows sputtering yield. However, the sputtering yield $Y(E, \theta)/Y(0)$ on the vertical axis is normalized with the sputtering yield $Y(0)$ when the angle of incidence of the ion beam $\theta$ is 0.

As shown in FIG. 2, the sputtering yield has a dependency on the angle of incidence of the beam. The sputtering yield increases as the angle of incidence of the beam $\theta$ increases over a range in which the angle of incidence of the beam $\theta$ (angle which the normal of the plane of incidence forms with the beam) varies from 0 degrees to 80 degrees. Especially when the angle of incidence of the beam $\theta$ exceeds 50 degrees, the sputtering yield drastically increases and the sputtering yield reaches a maximum when the angle of incidence of the beam $\theta$ is approximately 80 degrees. When the angle of incidence of the beam $\theta$ exceeds 80 degrees, the sputtering yield drastically decreases. When the angle of incidence of the beam $\theta$ further increases, the sputtering yield falls below 1. Assuming that the angle of incidence of the beam when the sputtering yield is 1 (value corresponding to vertical incidence) is $\theta c$, $\theta c$ is approximately 87 degrees. When the angle of incidence of the beam exceeds $\theta c$, the sputtering yield becomes infinitesimal, making it substantially impossible to process the sample.

Figure 3:
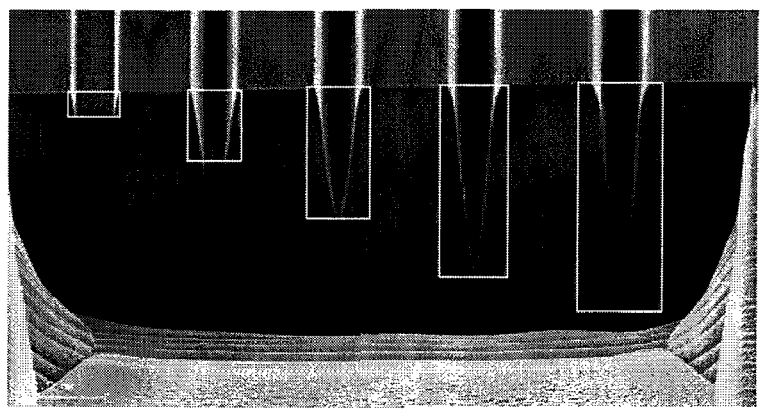
FIG. 3 shows an observation example of a cross section showing a relationship between a line width and processing depth for line creation.

When line processing is actually performed, V grooves are formed in the cross section of line processing due to this dependency of sputtering yield on the angle of incidence of the beam. FIG. 3 shows an example of line processing when the processing depth of line is changed with a line width of 1.5 μm. In this process, the surface of a flat sample is irradiated and scanned with an ion beam. Since the angle of incidence of the beam except at both ends of the line width is small in the beginning, a small concave part having an inclination at both ends of the line width is formed. As the processing advances (the groove deepens), the inclined planes at both ends expand toward the center of the line and the cross section of the line becomes a V groove. When the V groove is produced, the angle of incidence of the beam increases, the processing speed increases and the V groove deepens in a short time, but the angle of incidence of the beam drastically increases. Therefore, the surface is drastically shaved up to the angle of incidence of the beam with respect to the normal of the inclined plane of the concave part on the order of 80° and the V groove deepens, but processing gradually slows down thereafter and when the angle of incidence of the beam with respect to the normal of the inclined plane of the V groove reaches $\theta c$, processing of the V groove does not advance any further and the depth of the V groove is expected not to increase even if the processing time is further extended hereafter.

Next, sputtered particles are actually adsorbed to the side wall and disturb the processing, and therefore a relationship between the actual set value of the V groove and the depth of the actually processed V groove was examined. Table 1 shows conditions of the experiment.

TABLE 1

| Depth H | Condition of aspect ratio | | |
|---|---|---|---|
| | Width W | | |
| | (1) 0.5 μm | (2) 1.0 μm | (3) 1.5 μm |
| 1 μm | 2 | 1 | 0.7 |
| 3 μm | 6 | 3 | 2 |
| 5 μm | 10 | 5 | 3 |
| 10 μm | 20 | 10 | 7 |
| 20 μm | 40 | 20 | 13 |

Here, length of groove processing L: 20 μm, sample: Si, accelerating voltage: 40 kV and beam current: 3.9 nA were used for the processing beam. Furthermore, processing magnification: ×3000 (beam pitch: 11 nm), beam dwell time: Td=31s.

The processing time t is controlled using Expression 2 assuming that the sputtering yield $Y(0)=0.27$ (μm3/nC) when the angle of incidence of the ion beam $\theta$ with respect to a Si sample is 0.

[Formula 2]

$$t = \frac{H \cdot W \cdot L}{Ib \cdot Y(0)} \quad \text{(Expression 2)}$$

Figure 4:
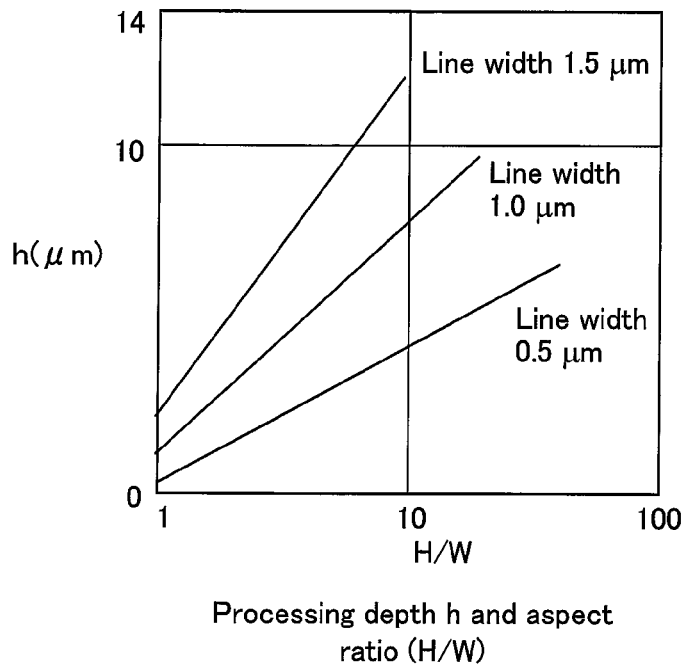
FIG. 4 shows a result of examining a relationship between a processing depth h and set aspect ratio (H/W).
Figure 5:
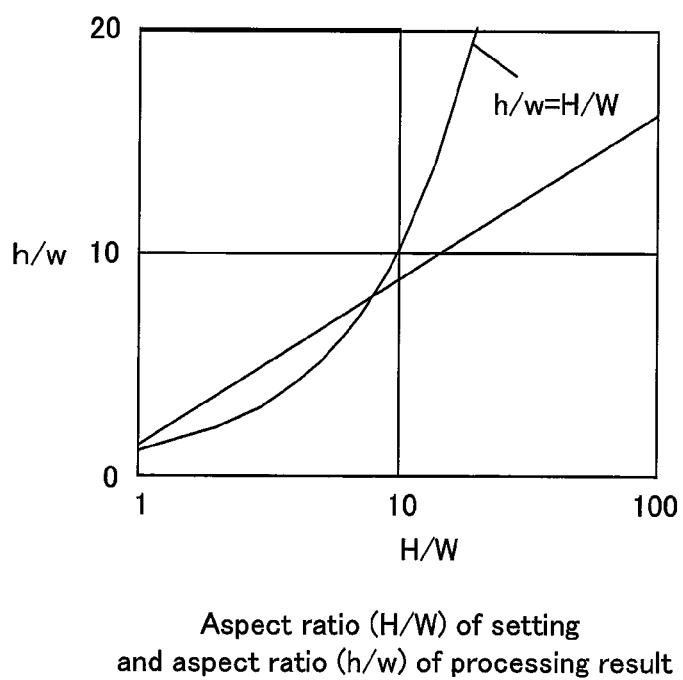
FIG. 5 shows a result of examining a relationship between the set aspect ratio (H/W) and an aspect ratio (h/w) obtained through actual processing.
Figure 11:
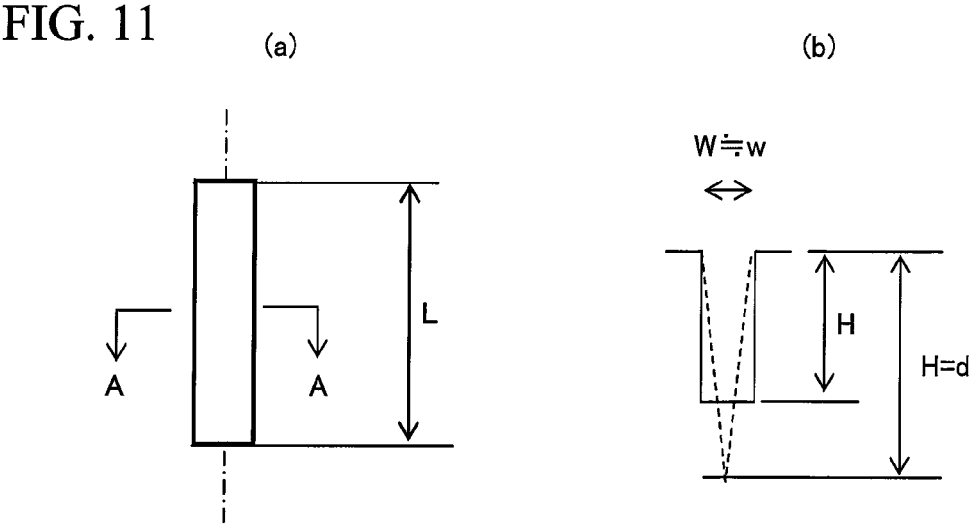
FIG. 11 shows a relationship between the set value H of the depth and set value W of the width of the V groove and the depth d of the actually formed V groove.

FIG. 4 is a graph showing the result of measuring the depth h of the V groove obtained through processing under the conditions in Table 1. It is appreciated from FIG. 4 that the processing depth h varies depending on the line width W. Furthermore, FIG. 5 is a graph showing the result of a conversion with respect to the aspect ratio (H/W) of the setting and the aspect ratio (h/w) of the processing result. Here, "H" is the set value of processing depth. The processing depth (set value) H and the actual line depth h (desired depth: depth in the vertical direction or height of small piece to be cut out) and actual depth d (desired depth: depth viewed from beam direction) have a relationship that when the angle of incidence of the beam is assumed to be 0°, if the processing conditions are set so that the surface is shaved to the depth H, the surface can actually be shaved to the depth h(=d) (see FIG. 11). From FIG. 5, Expression 3 is obtained assuming A: constant and α: constant.

[Formula 3]

$$\frac{h}{w} = A \cdot \mathrm{Ln}\left(\frac{H}{W}\right) + \alpha \quad \text{(Expression 3)}$$

Next, estimation of the amount of side wall redeposition in line processing will be explained. In the case of line (V groove) creation, as suggested by the experiment result, the gradual decrease of the processing depth is believed to be attributable to influences of redeposition. This is because particles sputtered on the bottom surface of processing pop out in proportion to $\cos\theta$ where $\theta$ is an angle with respect to the normal of the plane, but particles do not go out of the process area into the space and many particles collide with the side wall of processing and are adsorbed (redeposition).

Figure 6:
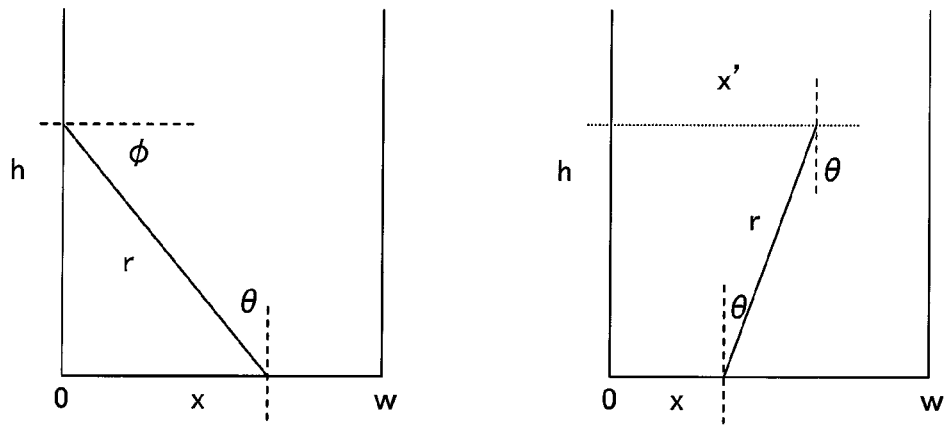
FIG. 6 illustrates a calculation model.

When the space is assumed to be infinite in the front-back direction of the surface of the present sheet in line processing, the space is symmetric in the front-back direction, and therefore redeposition can be considered with a two-dimensional line processing model shown in FIG. 6.

Assuming that the flux of the normal component of sputtered particles generated in the beam incident upon the processing hole is F0, F(h) which is the redeposition flux component of the surface normal at the height (depth) h from the bottom is expressed by Expression 4.

[Formula 4]

$$F(h) = \frac{F_0 \cdot h}{2} \int_0^w \frac{dr}{r^2} = \frac{F_0}{2}\left(1 - \frac{X}{\sqrt{X^2+1}}\right) \quad \text{(Expression 4)}$$

where $$X = \frac{h}{w}$$

Furthermore,

[Formula 5]

$$Q_{lost} = F_0 \cdot w - \int_0^h 2 \cdot F(h) \cdot dh \quad \text{(Expression 5)}$$

$$2 \cdot Q_{wall} = F_0 \cdot w - Q_{lost}$$

Therefore

[Formula 6]

$$Q_{lost} = F_0 \cdot h \cdot \left(\sqrt{1 + \left(\frac{w}{h}\right)^2} - 1\right) \quad \text{(Expression 6)}$$

$$= F_0 \cdot w \cdot \left(\sqrt{1 + X^2} - X\right)$$

[Formula 7]

$$2 \cdot Q_{wall} = F_0 \cdot \left\lfloor (w+h) - \sqrt{w^2 + h^2} \right\rfloor \quad \text{(Expression 7)}$$

$$= F_0 \cdot w \cdot \left(1 + X - \sqrt{1 + X^2}\right)$$

"Qwall" is a total amount of redeposition deposited on the wall when the depth of the hole is h. Furthermore, "Qlost" is a total amount of particles lost when the depth of the hole is h. The accumulative sum of Qlost is equivalent to the total volume lost due to processing≦depth.

[Formula 8]

$$\frac{H}{w} \propto \frac{\int_0^X Q_{lost} \, dX}{F_0 \cdot w} \quad \text{(Expression 8)}$$

Figure 7:
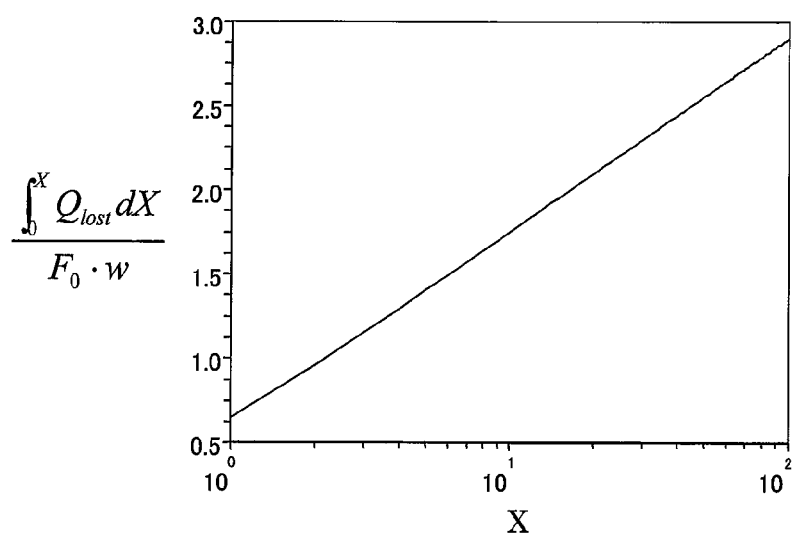
FIG. 7 shows a calculation result of an aspect ratio x and (accumulated amount of sputtering/aperture of hole) ratio.

The above described result can be expressed by a graph as shown in FIG. 7. It is appreciated from a comparison between FIG. 5 and FIG. 7 that FIG. 5 which is the result obtained by an experiment matches FIG. 7 which is the result obtained through a calculation. Therefore, it is appreciated that line (V groove) creation is performed according to Expression 9 due to influences of redeposition.

[Formula 9]

$$\frac{h}{w} = A \cdot \mathrm{Ln}\left(\frac{H}{W}\right) + \alpha \quad \text{(Expression 9)}$$

where, A: constant, α: constant.

Therefore, if constants A and α are determined assuming that the actual depth h of the V groove is a desired depth d (actual depth viewed from the radiation direction of the beam) and the actual width w of the V groove is a line width W, line creation can be controlled from the set values H and W, length of the line L, processing beam current Ib and a sputtering yield Y(0) of the sample at the angle of incidence of the beam of 0°.

Next, conditions under which the processing time reaches a minimum will be considered. The processing time t is expressed as Expression 10 assuming the beam current Ib and sputtering yield Y(0) at the angle of inclination of 0.

[Formula 10]

$$t = \frac{H \cdot W \cdot L}{Ib \cdot Y(0)} = \frac{w^2 \cdot \mathrm{Exp}\left(\frac{1}{A}\left(\frac{h}{w} - \alpha\right)\right) \cdot L}{Ib \cdot Y(0)} \quad \text{(Expression 10)}$$

where, W≦w is assumed in Expression 10.

Since the processing time has extreme values with the line width w, the minimum processing time is calculated by Expression 11.

[Formula 11]

$$\frac{\partial t}{\partial w} = 0 \quad \text{(Expression 11)}$$

Therefore, Expression 12 is obtained from Expression 11.

[Formula 12]

$$w \cdot \mathrm{Exp}\left(2 - \frac{\alpha}{A}\right) = H \quad \text{(Expression 12)}$$

Figure 8:
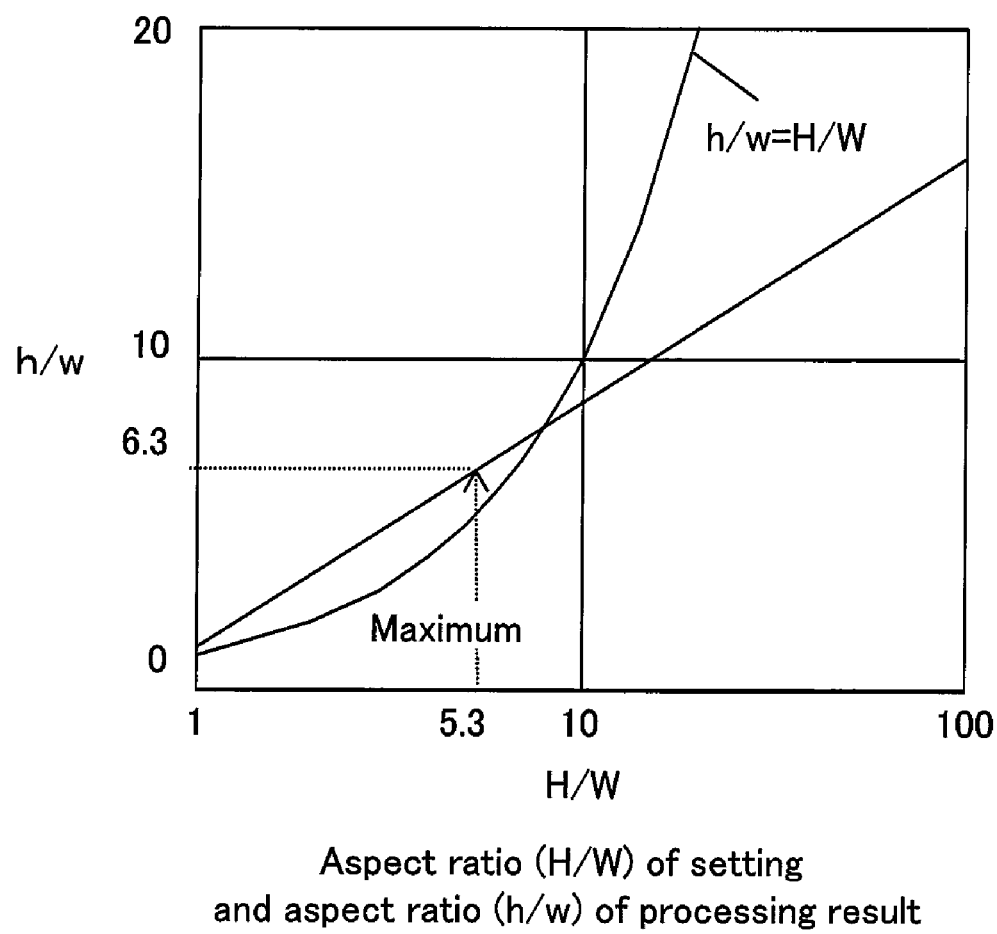
FIG. 8 shows a comparison between a relationship between the set aspect ratio (H/W) and the aspect ratio (h/w) obtained through actual processing and a relationship of H/W=h/w.

When the conditions under which the processing time t becomes a minimum are obtained from the experiment result, A=3.1303, α=1.0609. Therefore, A and α depend on the conditions of the experiment to a certain degree, but A≦3.13 and α≦1.06. This result shows that from Expression 9 and Expression 12, in line (groove) processing of length L, desired groove depth d=actual groove depth h, line width to be set W≦actual groove width w and the line depth to be set H obtains the relationship in the following expression. The result is shown in FIG. 8.

[Formula 13]

$$\frac{d}{w} = 6.3, \quad \frac{H}{W} \leq 8 \quad \text{(Expression 13)}$$

Here, preferably $\frac{H}{W} = 5.3$

Furthermore, it is appreciated that in line (groove) processing of length L, desired groove depth d=actual groove depth h, set line width W≦actual groove width w and the set line depth H have the relationship shown in Expression 14.

[Formula 14]

$$\frac{d}{w} \propto \mathrm{Ln}\left(\frac{H}{W}\right) \qquad \text{(Expression 14)}$$

Therefore, even when H/W changes from 10 to 100 in line processing, d/w only doubles and it is thereby appreciated from FIG. 8 that when the aspect ratio is 8 or greater, the processing becomes slower than the processing whereby the depth deepens in proportion to the processing time. Therefore, if the aspect ratio H/W is on the order of 8 or below, general processing becomes faster than the processing speed predicted from the sputtering yield Y(0) at the radiation angle of the beam 0° with respect to the sample.

α and A must be determined to control the groove depth d of the line to be actually processed and the aspect ratio controlled in a fastest state is on the order of H/W≦5.3.

<Configuration of Inclined Column Charged Particle Beam Apparatus>

Figure 9:
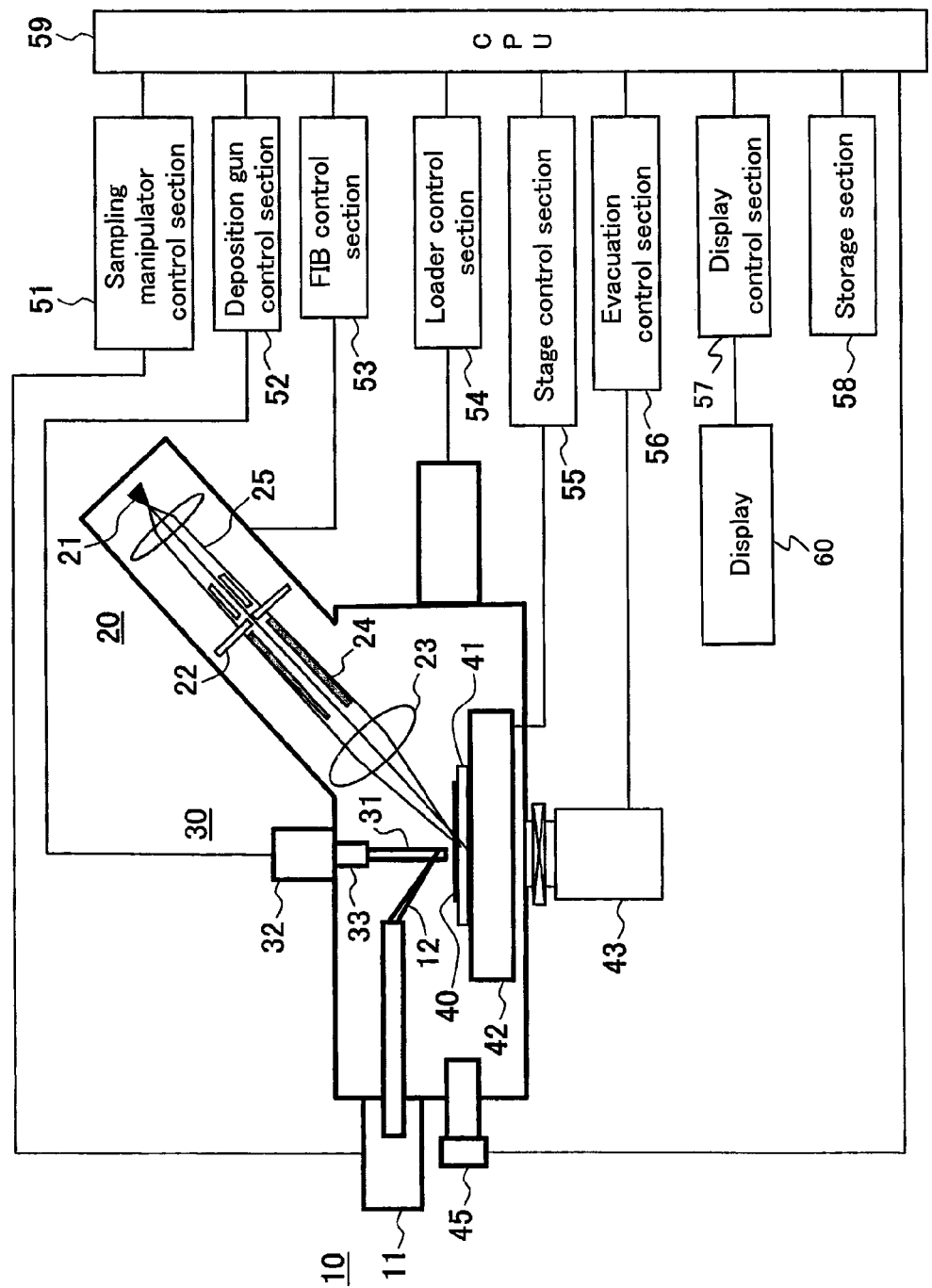
FIG. 9 shows a schematic configuration of the charged particle beam apparatus according to the present invention.

FIG. 9 shows a schematic configuration of an inclined column charged particle beam apparatus according to this embodiment of the present invention. As shown in FIG. 9, the inclined column charged particle beam apparatus is provided with a sampling manipulator 10, a focused ion beam (FIB) column 20, a deposition gun 30, a wafer holder 41 that holds a wafer 40 which is a sample, a stage 42 made up of four axes X, Y, Z, R (rotation), an evacuator 43 and a charged particle detector 45. The x-axis and y-axis are taken in the horizontal direction on the stage 42 and the z-axis is taken in the vertical direction.

The sampling manipulator 10 has a probe position controller 11 and a sampling probe 12. The FIB column 20 has an ion gun 21 made up of a Ga liquid metal ion source, a beam limitation aperture 22 that limits an ion beam 25, a lens system 23 that condenses the ion beam 25 and a deflector 24 for scanning the wafer with a beam. The optical axis of the FIB column 20 is inclined by 45° with respect to the Z-axis of the stage 42.

The deposition gun 30 has a nozzle 31, a nozzle position and temperature controller 32 and a deposition source reservoir 33. The deposition source reservoir 33 is filled with $W(CO)_6$.

The inclined column charged particle beam apparatus of this embodiment further has a sampling manipulator control section 51, a deposition gun control section 52, an FIB control section 53, a loader control section 54, a stage control section 55, an evacuation control section 56, a display control section 57, a storage section 58 and a CPU 59.

The sampling manipulator control section 51 controls the sampling manipulator 10, extracts a micro sample separated from the wafer and remounts the sample. The deposition gun controller 52 controls the deposition gun 30, performs temperature control over the gas source and control over the nozzle position. The FIB control section 53 controls the FIB column 20 and controls acceleration of an ion beam, beam current, focusing and deflection. The loader control section 54 controls loading and unloading of the wafer holder 41.

The stage control section 55 drives the stage 42 and controls the position thereof based on position information measured by a laser length measuring system. The stage 42 is a 4-axis stage that performs rectilinear movement in the X, Y, Z-axis directions and rotation around the Z-axis. In this embodiment, the laser length measuring system obtains position information, and can thereby improve positioning accuracy of sampling. Therefore, it is possible to reliably perform sampling of a target location from the wafer.

The evacuation control section 56 controls the evacuator 43. The display controller 57 displays an image obtained from a signal from the charged particle detector 45 synchronized with a scanning signal on a display 60. The storage section 58 stores images. The CPU 59 manages the entire inclined column charged particle beam apparatus in a concentrated manner. In processing, the CPU displays an area to be processed superimposed on the image displayed on the display 60, calculates processing control parameters and controls the processing.

According to the charged particle beam apparatus of this embodiment, when the user inputs a desired line segment length L and a depth d of a V groove, the CPU 59 calculates a set value H of the depth and a set value W of the width of the V groove according to Expression 9. The charged particle beam apparatus forms the V groove based on the set value H of the depth and the set value W of the width calculated by the CPU 59 as the length L of a line segment. When processing is performed for the processing time t according to Expression 15 assuming beam current Ib, line segment length L and sputtering yield Y(0) when the angle of incidence of the ion beam θ with respect to the sample is 0, the V groove having a desired depth d is formed.

[Formula 15]

$$t = \frac{H \cdot W \cdot L}{Ib \cdot Y(0)} \qquad \text{(Expression 15)}$$

Table 2 shows a comparison between conventional set items and set items of the present invention.

TABLE 2

Comparison between conventional set items and set items of the present invention

|  | Conventional Input value = set value | Present invention | |
|---|---|---|---|
|  |  | Input value | Set value |
| Length | L | L | L |
| Width | W | — | W (calculated value) |
| Depth | H | d (necessary depth) | H (calculated value) |
| Material | Y (0) | Y (0) | Y (0) |
| Result | Processing to necessary depth not obtained | Processing to necessary depth obtained in shortest time | |

<Method of Cutting Out Micro Piece>

Next, the method of cutting out a micro piece containing defects without splitting the wafer using the inclined column charged particle beam apparatus in FIG. 9 will be explained. The present invention performs V-shaped groove processing using the FIB column 20 having an optical axis inclined by θ degrees with respect to the sample surface. The present invention fixes the FIB column 20 and cuts out the micro piece through only the movement and rotation of the wafer and by only line segment (V groove) creation.

First, as shown in FIG. 10(a), suppose the optical axis 25A of the focused ion beam 25 exists on the xz plane. Furthermore, suppose the optical axis 25A of the focused ion beam 25 is inclined by 45 degrees with respect to the z-axis. By moving the sample wafer along the x-axis direction, V grooves 201 and 202 in the x-axis direction are formed. The V grooves 201 and 202 are formed in a direction perpendicular to the surface of the wafer. FIG. 10(b) is a cross-sectional view along the direction of an arrow B-B of FIG. 10(a). Both ends of the V grooves 201 and 202 have inclined planes 201a and 201b corresponding to the angle of inclination 45 degrees of the ion beam. Next, by moving the wafer along the y-axis direction, a V groove 203 in the y-axis direction is formed. FIG. 10(c) is a cross-sectional view along the direction of an arrow C-C of FIG. 10(a). The cross-section of the V groove 203 is inclined by 45 degrees with respect to the surface of the wafer.

Next, the sample wafer is rotated 180 degrees around the z-axis. As shown in FIG. 10(d), this causes the V groove 203 to become parallel to the y-axis and causes the V grooves 201 and 202 to become parallel to the x-axis. By moving the wafer along the y-axis direction, a V groove 204 in the y-axis direction is formed. FIG. 10(e) is a cross-sectional view along the direction of an arrow E-E of FIG. 10(d). The cross section of the V groove 204 is inclined 45 degrees with respect to the wafer surface.

FIG. 10(f) shows a micro piece 205 cut out by the four V grooves 201, 202, 203 and 204.

To actually cut out the micro piece 205, the sampling probe 12 is used as explained with reference to FIG. 9. Before completely separating off the micro piece 205 by the four V grooves 201 and 202, 203, 204, the tip of the sampling probe 12 is adhered to the top surface of the micro piece 205 using tungsten deposition. In this way, the micro piece 205 is completely separated off with the micro piece 205 held by the sampling probe 12. Since the micro piece 205 actually never tips over during groove processing, the tip of the sampling probe 12 may also be to adhered to the top surface of the micro piece 205 after completely separating off the micro piece 205.

In this way, a prism-like micro piece 205 having an isosceles triangular cross section is obtained by forming the rectangle-shaped V groove.

In the processing of extracting the micro piece (sampling processing), the CPU calculates processing set values from input parameters of processing, displays the area where the beam is actually irradiated, superimposed on the scanned ion image displayed on the display 60. Since this processing calculates and determines the line width W from the depth d of the required line, the line provided with the width W as the calculation result is displayed and the process area is revealed.

Figure 12:
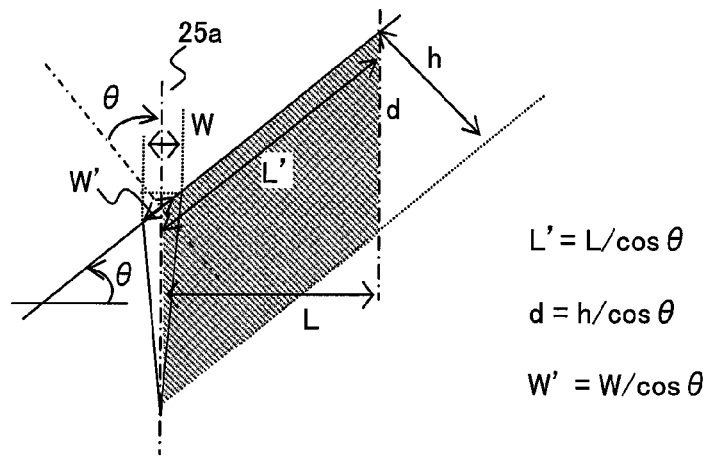
FIG. 12 shows a relationship between the size viewed from the beam radiation direction and the size on the sample surface.

Furthermore, the cross section of line processing of a set depth H along A-A in FIG. 11(a) is a V groove having a depth h=d with the center line of a width W≦w (processed line width) as a vertex as shown in FIG. 11(b). In order to display the scanned ion image with the process area actually irradiated with the beam superimposed thereon, the size of the irradiated area when viewed from the direction of incidence of the beam needs to be displayed. According to this definition, the processing depth becomes a depth with respect to the direction of incidence of the beam. FIG. 12 shows this relationship in the case where the sample is inclined by θ with respect to the direction of incidence of the beam. When processing a line segment having a length L, line width W and depth d viewed from the direction of incidence of the beam, the corresponding line segment on the sample has a line length L/cos(θ), line width W/cos(θ) and depth from the sample surface h=d×cos(θ). Since the size of the micro piece to be sampled is naturally displayed in the size on the sample, the display of the process area is calculated according to this rule.

Figure 13:
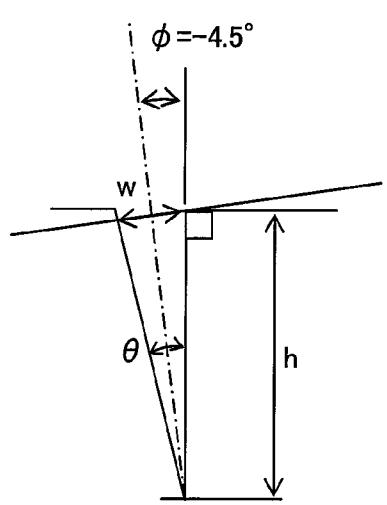
FIG. 13 illustrates how a right-angled vertical angle is obtained with the V groove.

As shown in FIG. 13, since the angle θ of the V groove is calculated as 9° from Expression 13, if processing is performed by inclining the sample stage by φ=−4.5° (assuming that the relative angle between the sample and the processing beam is −4.5°) as shown in FIG. 13 by taking the angle of the V groove into consideration, it is possible to realize extraction of a sample at a right-angled vertical angle.

<Screen Display During Sampling>

Figure 10:
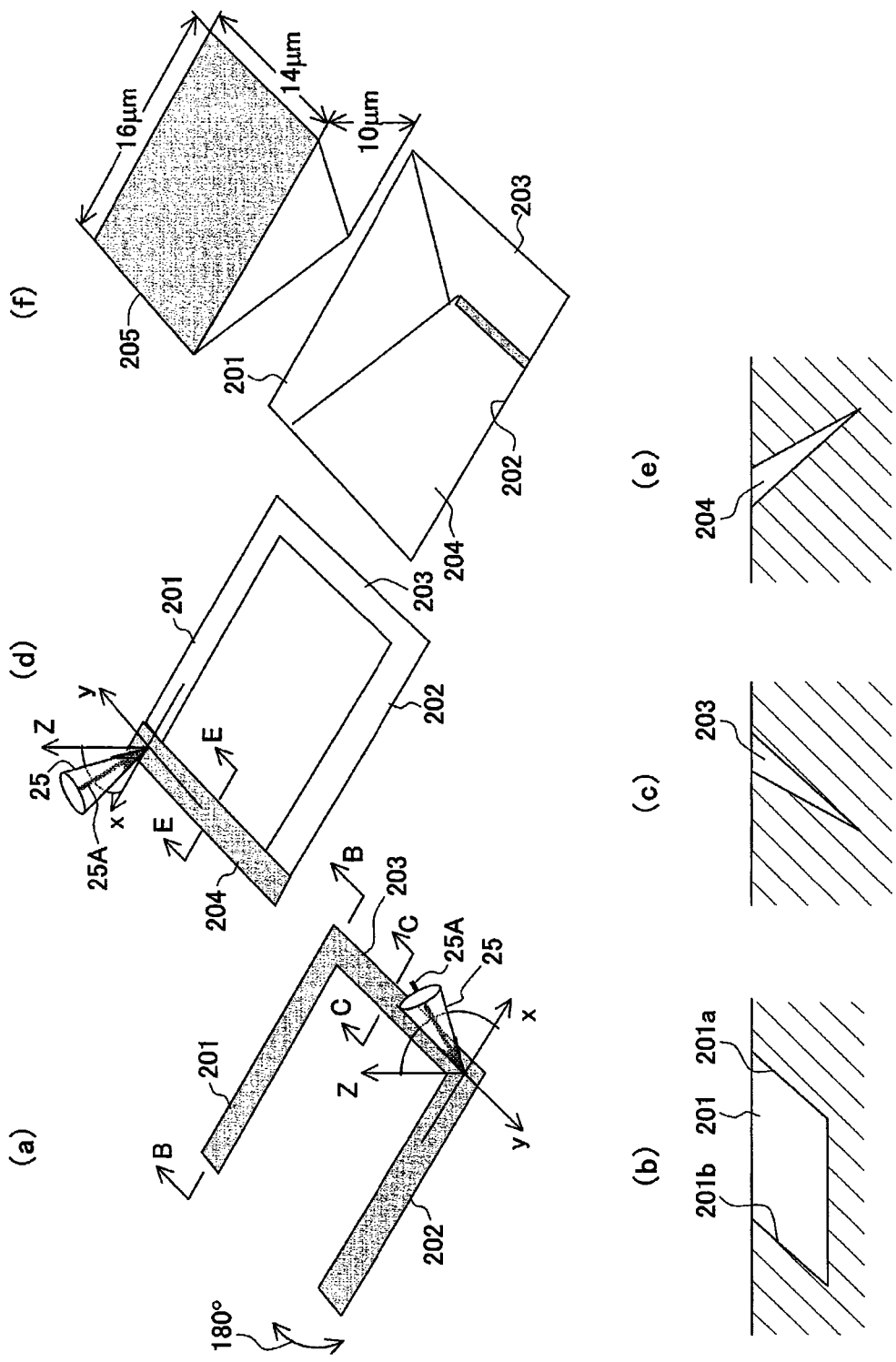
FIG. 10 illustrates a method of cutting out a micro sample with a rectangle-shaped V groove.

Hereinafter, an embodiment of display for sampling will be explained. The micro piece 205 in the isosceles triangular prism shape having the cross section as shown in FIG. 10(f) is obtained by performing line processing in the above described rectangle-shaped frame and forming V grooves around the rectangle. However, since the cross section of line processing to the depth H is an isosceles triangular prism having the center line of the width W as the vertex and the cross section is a V groove, if processing is performed with a beam inclined by 45° with respect to the sample shown in FIG. 10, an isosceles triangle having an angle acuter than the right angle is obtained instead of an isosceles right triangle.

The solution for this problem is complicated, but various methods are available, and since there is regularity, the CPU calculates the regularity and displays the result on a screen in an easy-to-see manner. As an example, a case where the isosceles triangular prism in FIG. 10(f) having a size of Lx=14 μm, Ly=16 μm and h=10 μm is cut out as the micro piece will be explained.

Figure 14:
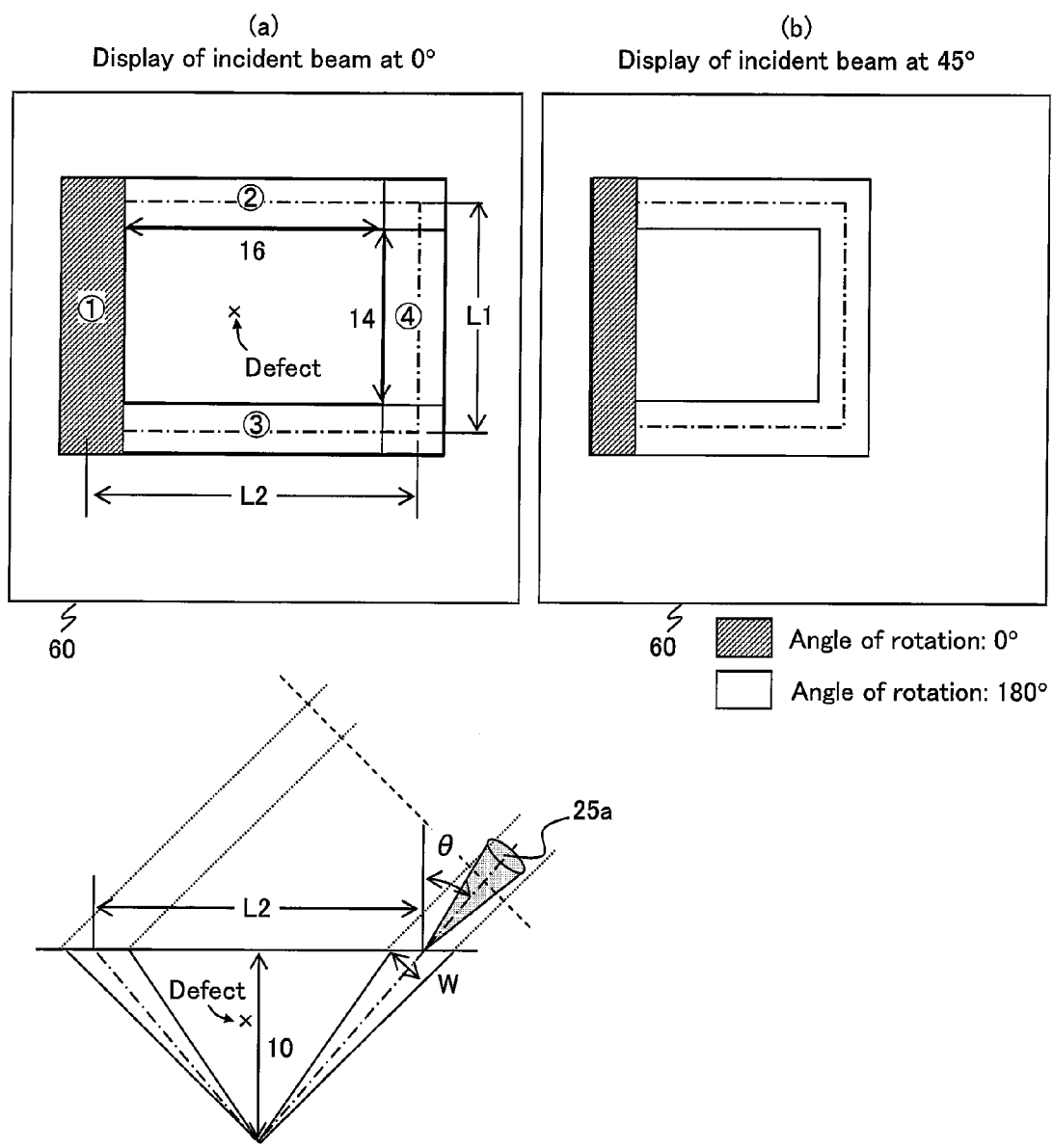
FIG. 14 illustrates a processing setting for sampling a small piece using a column apparatus inclined with respect to a sample using the present invention.

The table in FIG. 14 shows input values necessary for sampling. However, from the condition that the V grooves intersect with each other, the length in the beam inclination direction is determined from the sample height (L2=2×h×tan(θ)=20 μm).

To set the height of the micro piece to h=10 μm, since the beam is inclined by θ=45° with respect to the normal of the sample surface in the Ly (horizontal) direction, if the setting is changed to a setting whereby the sample is viewed from the beam, the depth of the V grooves 201 and 202 from the surface is 10/cos(θ)=14.1 μm.

Therefore, to obtain a desired processing depth d=14.1 μm, the set value W of the width and the set value H of the depth of the V grooves 201 and 202 are W=2.2 μm and H=11.9 μm from the expression of Formula 17.

The vertical length L1 of the frame shown in FIG. 14 is L1=16.2 μm obtained by adding the width W of the V groove 201 to the vertical length Lx=14 μm of the micro piece. Similarly, the necessary processing depth of the V groove 203 is d=14.1 μm. Therefore, the set value W of the width and the set value H of the depth of the V groove 203 are W=2.2 μm and H=11.9 μm from Expression 13.

With regard to the horizontal length L2 of the frame shown in FIG. 14, the V grooves do not intersect with each other unless L2=2×h×tan(θ)=20 μm because the micro piece is an isosceles triangular prism with h=10 μm. Since the beam is inclined by θ=45° in the Ly (horizontal) direction with respect to the normal of the sample surface, L2=20×cos(θ)=14.1 μm. In this case, the horizontal length Ly of the micro piece extracted is Ly=L2−W/cos(θ)=16.8 μm. The dimension of the micro piece 205 extracted turns out to be 14 μm×16 μm×10 μm. Here, the height is 10 μm. Table 3 shows the size of the display with the inclination of the beam taken into consideration.

TABLE 3

Set values of micro piece (14 μm × 16 μm × 10 μm)
displayed on display Angle of beam inclination (θ = 45°),
Ly (L2) axial direction

| | Set value | | | Display: φ = 0° | | Display: φ = 180° | |
|---|---|---|---|---|---|---|---|
| Processing order | Angle of rotation of stage φ | W (μm) | H (μm) | L1 (μm) | L2 (μm) | L1 (μm) | L2 (μm) |
| i) | 0° | 2.2 | 11.9 | 16.2 | (2.2) | 16.2 | (2.2) |
| ii) | 180° | 2.2 | 11.9 | (2.2) | 14.1 | (2.2) | 14.1 |
| iii) | 180° | 2.2 | 11.9 | (2.2) | 14.1 | (2.2) | 14.1 |
| iv) | 180° | 2.2 | 11.9 | 16.2 | (2.2) | 16.2 | (2.2) |

Since the width W is a width viewed from the beam, when L1 and L2 shown in Table 3 are used as the frame shown in FIG. 14(b), the area provided with the width W using the frame as the center axis becomes the actual beam irradiated area. FIG. 14(a) is a top view of the sample.

Table 3 is generated when the size of the micro piece (e.g., isosceles triangular prism in size of Lx=14 μm, Ly=16 μm, h=10 μm in FIG. 10(f)) is inputted to the display 60 in accordance with the magnification of the sample image obtained through ion beam scanning, and the frame and the beam irradiated area having the width W centered on the frame are superimposed on the sample image obtained through ion beam scanning and displayed as shown in FIG. 14. Furthermore, the area is decomposed into, for example, four line segment areas so that the four corners overlap each other, information such that the rotation angle of the stage φ=0°, 180° or the like is added and the processing order is displayed.

The processing information necessary for processing of each line segment is the beam irradiated area (L×W), depth H and processing time. The processing time of each line segment is calculated by substituting the H, W values of each line segment and beam current Ib processed as the sputtering yield Y(0) when the angle of incidence of the ion beam θ with respect to the sample is 0 into Expression 15.

Assuming the sputtering yield Y(0)=0.27 (μm3/nC) when the angle of incidence of the ion beam θ with respect to the Si sample is 0, the processing time for extracting the micro piece with a beam current of 20 nA with the sum of processing times of the respective line segments is approximately 5 minutes. As a result, a micro piece in size (vertical Lx=14 μm, horizontal Ly=16 μm, height h=10 μm) is separated from the sample.

The embodiment of the present invention uses an ion beam inclined with respect to the normal of the sample to form V grooves. However, any configuration can be adopted for the charged particle beam apparatus as far as an ion beam inclined with respect to the normal of the sample can be generated. In the example of FIG. 9, the charged particle beam apparatus is provided with the FIB column 20 having the optical axis inclined with respect to the z-axis of the stage 42. However, as will be described later, a stage having the function of inclining the sample may be used instead of providing the inclined FIB column 20.

Furthermore, the above described example uses the ion beam inclined by 45 degrees with respect to the normal of the sample, but an ion beam inclined by a different angle with respect to the normal of the sample may also be used. For example, an ion beam inclined by 30 degrees or 60 degrees with respect to the normal of the sample may be used.

Next, a sampling method using line (V groove) creation will be explained, which uses a charged particle beam apparatus capable of tilting a stage to which a sample is fixed with respect to the column instead of the inclined column in FIG. 9.

Figure 15:
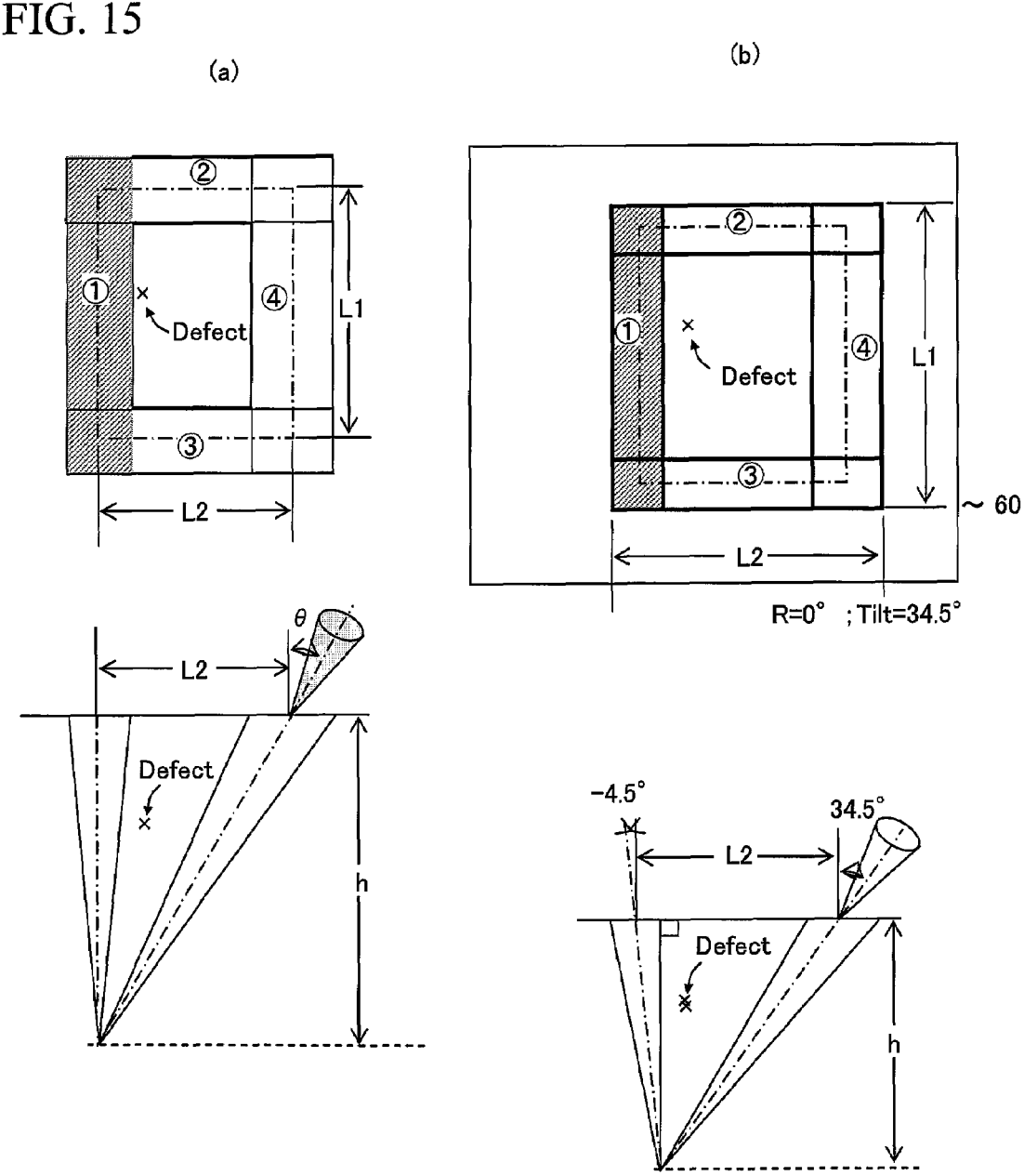
FIG. 15 illustrates a processing setting for sampling a small piece using an apparatus having a stage that can be inclined using the present invention.

Though various processing shapes may be considered as shapes of the micro piece, a sampling method when the angle of stage inclination θ=30° is shown in FIG. 15(a). An embodiment of sampling of a micro piece of a triangular prism in a size (vertical Lx=10 μm, horizontal Ly=7.8 μm, height h=20 μm) shown in FIG. 15(a) will be explained. Suppose the stage inclination direction is Ly(L2) axial direction.

A triangular prism is selected as the shape of the micro piece extracted through sampling and the size (vertical Lx=10 μm, horizontal Ly=12 μm, height h=20 μm) is inputted. Here, since the height h of the micro piece=20 μm, the initial value of Ly is assumed to be h×tan(θ) from the condition under which the V grooves intersect with each other.

In the case of the line segment with height h=20 μm, angle of stage inclination θ=0° of the micro piece shown in FIG. 15(a), h=20 μm, and W=3.2 μm and H=16.8 μm are obtained using Formula 17, while in the case of angle of stage inclination θ=30°, since d=h/cos(θ)=23 μm, W=3.7 μm and H=19.4 μm are obtained using Expression 13.

The size L1×L2 of the frame displayed on the display is L1=Lx+3.7=13.7, L2=Ly=h×tan(θ)=11.5 μm when the angle of stage inclination 0°. On the other hand, L1=13.7, L2=Ly×cos(θ)=10 μm when the angle of stage inclination 30°. The size of the display in consideration of the inclination of the beam is shown in Table 4.

TABLE 4

Set values displayed on display
Angle of stage inclination (θ), Ly (L2) axial direction

| | Set value | | | Display: θ = 0° | | Display: θ = 30° | |
|---|---|---|---|---|---|---|---|
| Processing order | Angle of stage inclination θ | W (μm) | H (μm) | L1 (μm) | L2 * cos θ (μm) | L1 (μm) | L2 * cos θ (μm) |
| i) | 0 | 3.2 | 16.8 | 13.7 | (3.2) | 13.7- | (2.7) |
| ii) | 30 | 3.7 | 19.4 | (3.7) | 11.5 | (3.7) | 10 |

TABLE 4-continued

| | Set values displayed on display Angle of stage inclination (θ), Ly (L2) axial direction | | | | | | |
|---|---|---|---|---|---|---|---|
| | Set value | | | | Display: θ = 0° | | Display: θ = 30° |
| Processing order | Angle of stage inclination θ | W (μm) | H (μm) | L1 (μm) | L2 * cos θ (μm) | L1 (μm) | L2 * cos θ (μm) |
| iii) | 30 | 3.7 | 19.4 | (3.7) | 11.5 | (3.7) | 10 |
| iv) | 30 | 3.7 | 19.4 | 13.7 | (4.2) | 13.7 | (3.7) |

Since the width W is a width viewed from the beam, when L1 and L2 shown in bold letters in Table 4 are used as the frame shown in FIG. 15(a) and the area is displayed using items in parentheses in Table 4 as the line width W using the frame as the center axis, the displayed area is the actual beam irradiated area.

The area is displayed superimposed on the sample image obtained through ion beam scanning. Furthermore, as shown in FIG. 15(a), the area is decomposed into four line segment areas so that, for example, the four corners overlap each other and information such as the angle of stage inclination θ=0°, 30° is added and the processing order is displayed.

The processing information necessary for processing of each line segment is the beam irradiated area (L×W) and depth H and processing time. The processing time of each line segment is calculated by substituting the H and W values of each line segment and the beam current Ib processed as the sputtering yield Y(0) when the angle of incidence of the ion beam θ with respect to the sample is 0 into above described Expression 15.

Assuming the sputtering yield Y(0)=0.27 (μm3/nC) when the angle of incidence of the ion beam θ with respect to the Si sample is 0, the processing time for extracting the micro piece with a beam current of 20 nA with the sum of the processing times of the respective line segments is approximately 10 minutes. As a result of this processing, a micro piece in a size (vertical Lx=10 μm, horizontal Ly=7.8 μm, height h=20 μm) is separated from the sample.

In the micro piece extracted from Table 4, the right angle part of the right triangular prism is more obtuse than the right angle. In order to change the vertical angle to the right angle, as shown in FIG. 15(b), processing is performed with the inclination of the stage set to −4.5° in the processing order i) in Table 4. Since the display in the irradiated area in this case is cos(−4.5°)=0.997, the display may be the same as 0°.

Furthermore, as is appreciated from FIG. 15(a), the vertical angle part of the right triangular prism is acuter than 30°. In order to change this to 30°, processing is performed by setting the angle of inclination of the stage to 34.5° as shown in FIG. 15(b). When processing is performed in this way, a micro piece of right triangular prism in a size (vertical Lx=10 μm, horizontal Ly=11.5 μm, height h=20 μm) with a vertical angle 30° can be separated from the sample.

In the case of the line segment with height h=20 μm, angle of stage inclination θ=−5° of the micro piece shown in FIG. 15(b), h=20 μm, and W=3.2 μm and H=16.9 μm are obtained using Formula 13, while in the case of angle of stage inclination θ=35°, since d=h/cos(θ)=24.4 μm, W=3.9 μm and H=20.5 μm are obtained using Expression 13.

The size L1×L2 of the frame displayed on the display is L1=Lx×cos(θ)+3.9=13.9, L2=Ly+3.2/2+3.9/2/cos(35°)= 15.5 μm when the angle of stage inclination θ=−5°. On the other hand, L1=13.9, L2=15.5×cos(θ)=12.7 μm when the angle of stage inclination θ=35°. Table 5 shows the size of display with the inclination of the beam taken into consideration.

TABLE 5

| | Set value displayed on display Angle of stage inclination (θ), Ly (L2) axial direction | | | | | | |
|---|---|---|---|---|---|---|---|
| | Set value | | | | Display: θ = −5° | | Display: θ = 35° |
| Processing order | Angle of stage inclination θ | W (μm) | H (μm) | L1 (μm) | L2 * cos θ (μm) | L1 (μm) | L2 * cos θ (μm) |
| i) | −5 | 3.2 | 16.9 | 13.9 | (3.2) | 13.9 | (2.6) |
| ii) | 35 | 3.9 | 20.5 | (3.9) | 15.5 | (3.9) | 12.7 |
| iii) | 35 | 3.9 | 20.5 | (3.9) | 15.5 | (3.9) | 12.7 |
| iv) | 35 | 3.9 | 20.5 | 13.9 | (4.7) | 13.9 | (3.9) |

Since the width W is the width viewed from the beam, when L1 and L2 shown in Table 5 are used as the frame shown in FIG. 15(b) and the area provided the width W using the frame as the center axis is the actual beam irradiated area.

As shown in FIG. 15(b), the area is displayed superimposed on the sample image obtained through ion beam scanning. Furthermore, as shown in FIG. 15(b), the area is decomposed into four line segment areas so that, for example, the four corners overlap each other and information such as the angle of stage inclination θ=5°, 35° is added and the processing order is displayed.

The processing information necessary for processing of each line segment is the beam irradiated area (L×W) and depth H and processing time. The processing time of each line segment is calculated by substituting the H and W values of each line segment and the beam current Ib processed as the sputtering yield Y(0) when the angle of incidence of the ion beam θ with respect to the sample is 0 into above described Expression 15. Assuming the sputtering yield Y(0)=0.27 (μm3/nC) when the angle of incidence of the ion beam θ with respect to the Si sample is 0, the processing time for extracting the micro piece with a beam current 20 nA with the sum of the processing times of the respective line segments is approximately 12 minutes. As a result, a micro piece whose vertical angle is right-angled in a size (vertical Lx=10 μm, horizontal Ly=12 μm, height h=20 μm) is separated from the sample.

"x" shown in the micro piece in FIG. 15(a) and FIG. 15(b) indicates a defect position of the device and in view of the process of creating a thin-lamina sample including "x" from the sampled micro piece, FIG. 15(b) is more convenient for sampling and for creation of thin laminas.

In this way, there are various processing methods for sampling a micro piece, and when a sample shape in a required size is inputted, it is possible for the CPU to calculate processing conditions and a procedure necessary for sampling and display the processing conditions and procedure as shown in FIG. 15(b), display the area in which the beam is actually irradiated on a screen according to the state of the stage and process the area. For this reason, it is possible to perform sampling of a micro piece by performing proceeding according to instructions on the screen without worries no matter how complicated the processing may be.

Furthermore, though the processing time t is expressed by Expression 15, since H>>W, L>>W according to the present invention, the processing time t is proportional to H×L. On the other hand, since H>>W, L>>W cannot be set in the conventional processing, the processing time t is proportional to H×W×L. That is, while the processing time for the size of a micro piece expands in terms of area according to the present invention, the processing time increases in terms of volume according to the conventional method. For this reason, the processing time can be shortened.

As described above, the present invention allows a micro piece to be sampled from a sample through only V groove processing and can thereby realize sampling processing with one type of processing beam. That is, the set value W of the width and set value H of the depth of the V groove are substantially constant from start to end of the processing.

Furthermore, according to the present invention, when a desired depth d is given in V groove processing, the set value H of the depth and set value W of the width of the V groove can be calculated so as to minimize the processing time. Therefore, the V groove can be processed simply and efficiently. Furthermore, since the processing volume in V groove processing is smaller than that of rectangular grooves, sampling can be realized even with a small beam current and in a short time.

Furthermore, according to the present invention, the apparatus provided with a column which is inclined with respect to a wafer can realize sampling of a micro piece containing defects using the rotation function of the stage only once without splitting the wafer and is thereby suitable for sampling automation.

What is claimed is:

1. A charged particle beam processing apparatus that processes a sample using a charged particle beam, comprising:
a stage that moves the sample in a desired axial direction;
a charged particle beam column that radiates a charged particle beam onto the sample;
a control section that controls the charged particle beam column; and
a calculation section that calculates a set value H of a depth for line creation (V groove) and a set value W of a width for the line creation (V groove) from an inputted desired line segment length L and a desired depth d for the line creation (V groove),
wherein the calculation section calculates a condition that minimizes a processing time t based on an arithmetic expression for a processing time t expressed by the set value H of the depth for the line creation and the set value W of the width for the line creation, length L for the line creation, sputtering yield Y(0) of matter and beam current Ib and thereby obtains the set values H and W, and
the control section causes the charged particle beam to be radiated onto the surface of the sample based on the set values H and W calculated by the calculation section and the length L for the line creation so as to form V grooves on a surface of the sample.

2. The charged particle beam processing apparatus according to claim 1, wherein the calculation section sets the set value W of the width and the set value H of the depth for the line creation determined from the desired line depth d so that a ratio of H/W becomes constant.

3. The charged particle beam processing apparatus according to claim 1, wherein the arithmetic expression for the processing time t is expressed by the following expression:

$$t = \frac{H \cdot W \cdot L}{Ib \cdot Y(0)}. \quad \text{[Formula 1]}$$

4. The charged particle beam processing apparatus according to claim 3, wherein the calculation section sets when the processing time t takes a minimum value with a line width w=W as a minimum processing time and the processing time t is expressed by the following expression assuming A and α are predetermined constants:

$$t = \frac{w^2 \cdot \operatorname{Exp}\left(\frac{1}{A}\left(\frac{d}{w} - \alpha\right)\right) \cdot L}{Ib \cdot Y(0)}. \quad \text{[Formula 2]}$$

5. The charged particle beam processing apparatus according to claim 4, wherein the calculation section sets the predetermined constants A and α as A≦3.1 and α≦1 respectively.

6. The charged particle beam processing apparatus according to claim 5, wherein the calculation section calculates the set value H of the depth for the line creation (V groove) and the set value W of the width for the line creation (V groove) using the following expression:

$$\frac{d}{W} \cong 6.3, \quad \frac{H}{W} \leq 8, \quad \frac{d}{W} \propto \operatorname{Ln}\left(\frac{H}{W}\right). \quad \text{[Formula 3]}$$

7. The charged particle beam processing apparatus according to claim 5, wherein the calculation section calculates the set value H of the depth for the line creation (V groove) and the set value W of the width for the line creation (V groove) using the following expression:

$$\frac{d}{W} \cong 6.3, \quad \frac{H}{W} \cong 5.3. \quad \text{[Formula 4]}$$

8. The charged particle beam processing apparatus according to claim 1, further comprising a display control section that displays a process area where the charged particle beam is irradiated onto the sample superimposed on the sample image on a display section based on the line width W and the length L for line creation calculated from the desired depth d.

9. The charged particle beam processing apparatus according to claim 8, wherein the display control section performs decomposition into four parts of line (V groove) creation in response to specifications of a frame of the process area and the desired line depth h, displays sequence of line (V groove) creation on the display section and allows processing of the sample according to the order.

10. The charged particle beam processing apparatus according to claim 8, wherein the display control section determines a frame necessary for the sampling in response to specifications of the desired line depth h (=height of a micro piece) of the micro piece to be sampled, radiation angle θ of the charged particle beam with respect to the sample and a size L of the micro piece in a direction perpendicular to the radiation direction of the charged particle beam, decomposes the frame into line segments using the frame as a center axis of the width W, superimposes a beam irradiated area viewed from the charged particle beam on a scanned image of the charged particle beam and displays the image on the display section.

11. The charged particle beam processing apparatus according to claim 8, wherein the calculation section decomposes the process area into line segments necessary for the sampling in response to specifications of the desired line depth h (=height of the micro piece) of the micro piece to be sampled, radiation angle θ of the charged particle beam with respect to the sample and the size L of the micro piece in a direction perpendicular to the radiation direction of the charged particle beam, determines a desired depth d of each line segment (=depth viewed from the radiation direction), calculates the set value W of the width and the set value H of the depth according to the arithmetic expression and determines the processing time t.

12. The charged particle beam processing apparatus according to claim 1, wherein the charged particle beam column is inclined by a predetermined angle with respect to the stage, and the control section causes the charged particle beam to be radiated onto the sample from a first radiation direction, then rotates the stage and causes the charged particle beam to be radiated onto the sample from a second radiation direction opposite to the first radiation direction.

13. A charged particle beam processing apparatus that processes a sample using a charged particle beam, comprising:
a stage that moves the sample in a desired axial direction;
a charged particle beam column that radiates a charged particle beam onto the sample;
a control section that controls the charged particle beam column;
a display control section that displays a sample image on a display section; and
a calculation section that calculates a set value of a depth H for line creation (V groove) and a set value of a width W for the line creation (V groove) from an inputted desired line segment length L (length when viewed from an radiation direction) and a desired depth d for the line creation (depth when viewed from the radiation direction),
wherein the calculation section calculates a condition that minimizes a processing time t based on a following arithmetic expression indicating the processing time t expressed by the depth H of the groove, width W of the V groove, length L of the V groove and sputtering yield Y(0) of matter and beam current Ib and thereby determines the set values H and W, $$t = \frac{H \cdot W \cdot L}{Ib \cdot Y(0)} \quad \text{[Formula 5]}$$

the time obtained by the arithmetic expression is designated as the processing time t,
the control section causes the charged particle beam to be radiated onto a process area displayed by the length L and the width W for the line creation for the processing time t and performs linear (V groove) creation of length L, width W, depth d for the line creation as a result of the radiation, and
the display control section superimposes the process area expressed by the width W and the length L together with the depth H, the line width W and the value of length L for the line creation which are the set values on the sample image and displays the area on the display section.

14. The charged particle beam processing apparatus according to claim 13, wherein the calculation section calculates a desired depth d viewed from the beam radiation direction when an radiation angle of the charged particle beam is assumed to be θ as d=h/cos θ based on the inputted desired line depth h,
the calculation section calculates as set values the depth H and the line width W that satisfy a following arithmetic expression or that satisfy a log approximation function where H/W is a variable, $$\frac{d}{W} \propto \mathrm{Ln}\left(\frac{H}{W}\right) \quad \text{[Formula 6]}$$

furthermore, when the length for line creation (V groove) on the sample is assumed to be L', the calculation section calculates the length L viewed from the radiation direction from L=L'·cos θ and assumes the length L as a set value.

15. A charged particle beam processing apparatus that processes a sample using a charged particle beam, comprising:
a stage that moves the sample in a desired axial direction;
a charged particle beam column that radiates a charged particle beam onto the sample;
a control section that controls the charged particle beam column;
a calculation section that calculates a set value of a depth H for line creation (V groove) and a set value of a width W for the line creation (V groove) from an inputted desired line segment length L and a desired depth d (depth when viewed from the radiation direction) for the line creation using a following expression, $$\frac{d}{W} \cong 6.3, \; \frac{H}{W} \cong 5.3 \quad \text{[Formula 7]}$$

wherein the control section causes the charged particle beam to be radiated onto the surface of the sample based on the set values H and W calculated by the calculation section and the length L for the line creation so as to form V grooves on the surface of the sample.

16. The charged particle beam processing apparatus according to claim 15, further comprising a display control section that displays the process area in which the charged particle beam is irradiated onto the sample, superimposed on the sample image on the display section based on the line width W and length L for the line creation calculated from the desired line depth h.

* * * * *